(12) United States Patent
Sanchis et al.

(10) Patent No.: US 6,686,149 B1
(45) Date of Patent: Feb. 3, 2004

(54) **METHODS FOR OBTAINING NUCLEOTIDE SEQUENCES CODING FOR POLYPEPTIDES SPECIFICALLY ACTIVE FOR LARVAE OF *S. LITTORALIS***

(75) Inventors: Vincent Sanchis, Cambridge (GB); Didier Lereclus, Paris (FR); Ghislaine Menou, Paris (FR); Marguerite-Marie Lecadet, Paris (FR); Daniel Martouret, Saint-Cyr l'Ecole (FR); Raymond Dedonder, Chatenay Malabry (FR)

(73) Assignees: Institut Pasteur, Paris (FR); Institut National de la Recherche Agronomique, Paris (FR)

( * ) Notice: Subject to any disclaimer, the term of this patent is extended or adjusted under 35 U.S.C. 154(b) by 0 days.

(21) Appl. No.: 09/583,717

(22) Filed: May 30, 2000

Related U.S. Application Data

(63) Continuation of application No. 08/461,750, filed on Jun. 5, 1995, now Pat. No. 6,110,734, which is a continuation of application No. 08/251,622, filed on May 31, 1994, now abandoned, which is a continuation of application No. 08/094,382, filed on Jul. 21, 1993, now abandoned, which is a continuation of application No. 07/458,754, filed as application No. PCT/FR88/00292 on Jun. 9, 1988, now abandoned.

(30) Foreign Application Priority Data

Jun. 10, 1987 (FR) ............................................ 87 08090
May 6, 1988 (EP) ............................................ 88401121

(51) Int. Cl.[7] ........................ C12N 15/74; G01N 33/00; C07H 21/04; C07K 17/00
(52) U.S. Cl. .................... 435/6; 435/320.1; 435/252.3; 436/94; 536/23.71; 530/350
(58) Field of Search ............................ 435/320.1, 252.3; 536/23.71; 436/94; 530/350

(56) References Cited

U.S. PATENT DOCUMENTS

| | | | |
|---|---|---|---|
| 5,593,881 A | 1/1997 | Thompson et al. | 11/240.1 |
| 5,596,071 A | 1/1997 | Payne et al. | 530/350 |
| 5,602,032 A | 2/1997 | Liu et al. | 4354/252.31 |

FOREIGN PATENT DOCUMENTS

| | | | |
|---|---|---|---|
| EP | 0228838 | 7/1987 | C12N/15/00 |

OTHER PUBLICATIONS

Honigman et al., Gene, vol. 42 (1986), pp. 69–77.
Jaquet et al., Appln. Env. Mic., Appl. Env. Mic., vol. 53, No. 3 (Mar. 1987), pp. 500–504.
Klier et al., Mol. Biol. of Mic. Diff., Ninth Conf. (Sep. 1986), pp. 217–224.
Suggs et al., PNAS, vol. 78, No. 11 (Nov. 1981), pp. 6613–6617.
Webiko et al., DNA, vol. 5, No. 4 (1986), pp. 305–314.
Wong et al., J. Biol. Chem., vol. 258, No. 3 (Feb. 10, 1983), pp. 1960–1967.

*Primary Examiner*—Ethan Whisenant
*Assistant Examiner*—Joyce Tung
(74) *Attorney, Agent, or Firm*—Finnegan, Henderson, Farabow, Garrett & Dunner, L.L.P.

(57) ABSTRACT

This invention relates to a method for the cloning a polypeptide having larvicidal activity. In particular, the invention relates to vectors, bacterial strains and methods for the cloning and expression of the N-terminal region of a polypeptide toxic against the larvae of Lepidoptera of the Noctuidae family, preferably against *S.littoralis*.

1 Claim, 5 Drawing Sheets

METHODS FOR OBTAINING NUCLEOTIDE SEQUENCES CODING FOR POLYPEPTIDES SPECIFICALLY ACTIVE FOR LARVAE OF S. LITTORALIS

This is a continuation of application Ser. No. 08/461,750, now U.S. Pat. No. 6,110,734, filed Jun. 5, 1995, which is a con of Ser. No. 08/251,622, filed May 31, 1994, now abandoned, which is a con of Ser. No. 08/094,382, filed Jul. 21, 1993, now abandoned, which is a con of Ser. No. 07/458,754 filed Dec. 11, 1989, now abandoned, which is a 371 of PCT/FR88/00292 filed Jun. 9, 1988.

The subject of the invention is nucleotide sequences coding for polypeptides endowed with a larvicidal activity towards Lepidoptera.

It relates more particularly to agents, in particular nucleotide sequences, polypeptides or even vectors, or bacterial strains modified by these sequences and expressing polypeptides making it possible to prepare larvicidal compositions active against Lepidoptera, preferably against *Spodoptera littoralis* (hereafter *S.littoralis*) or *Mamestra brassicae* (hereafter designated by *M.brassicae*) or capable of transforming the plants to be treated in conferring on them this type of activity.

BACKGROUND OF THE INVENTION

It is known that most of the isolates of *B.thuringiensis* show a toxic activity with regard to larvae of more than a hundred species of Lepidoptera.

This activity results from the capacity of the strains of *B.thuringiensis* to synthesize, at the moment of sporulation, crystalline inclusions of protein nature, or δ-endotoxins, under the control of one or several types of gene.

It has been shown that the activity of these polypeptides is contained in the NH$_2$-terminal half or N-terminus of the protein.

The studies carried out have shown the high specificity of the δ-endotoxins towards larvae of a given species.

On account of this high specificity, many species of Lepidoptera, in particular of the family of the Noctuidae, react only weakly to commercial preparations of available *B.thuringiensis*.

It is so in particular for the species *S.littoralis*, a polyphagous insect which constitutes the principal parasite of cotton and other industrially important crops. Among these crops, mention should be made of maize, the castor oil plant, tobacco, the groundnut, fodder plants, such as clover or alfalfa, or also market garden produce such as the cabbage or the tomato.

Hence, one can imagine the interest of disposing of agents targeting specifically and effectively the family of the Noctuidae and in particular *S.littoralis* or *M.brassicae*.

The genes for δ-endotoxins hitherto identified do not code for a polypeptide preferentially active with regard to *S.littoralis*.

SUMMARY OF THE INVENTION

The search by the inventors for a sequence of nucleotides coding for a polypeptide preferably active against the Noctuidae, more especially against *S.littoralis*, has led them to study the natural isolates of two strains of *B.thuringiensis*, the larvicidal activity of which on *S.littoralis* appears to be higher than that of the industrial preparations made starting from other strains of *B.thuringiensis*.

The species in question are *aizawai* 7-29 and *entomocidus* 6-01.

The study of these isolates has made it possible to demonstrate the existence of several genes for δ-endotoxins of different structures and different specificities, of which two genes preferentially active against *P.brassicae* but not very active against the Noctuida of cotton and a gene inactive against *P.brassicae* and *S.littoralis*.

By studying the total DNA of these isolates and by carrying out appropriate hybridizations, followed by the cloning of the fragments identified by hybridization, the inventors have observed that it is possible to isolate nucleotide sequences implicated in genes for δ-endotoxins coding for polypeptides active, preferably, against *S.littoralis*.

Thus, the aim of the invention is to provide nucleotide sequences capable of coding for at least the NH$_2$-terminal part of a δ-endotoxin toxic against the Noctuidae and preferably against *S.littoralis* or *M.brassicae*.

It also has the aim of providing a polypeptide toxic with regard to the Noctuidae.

Furthermore, the invention relates to a procedure for obtaining such a sequence and a polypeptide showing the desired activity as well as the intermediate agents such as vectors and bacterial strains which can be utilized for obtaining the polypeptide.

In addition, the invention relates to the uses of these sequences and polypeptides for the development of larvicidal compositions with regard to the Noctuidae, in particular *S.littoralis* and for the transformation of the plants likely to be infected by these larvae.

The invention relates to a sequence of nucleotides coding for at least a part of the N-terminal region of a polypeptide toxic specifically against the larvae of Lepidoptera of the Noctuidae family, and preferably against *S.littoralis*, characterized by its capacity of hybridization with a gene capable of expressing a polypeptide toxic towards larvae of *S.littoralis*.

According to another aspect of the invention, the nucleotide sequence is characterized in that it is carried by a sequence of nucleotides of about 3 kb such as obtained by in vitro genetic recombination of sequences of nucleotides of *B.thuringiensis* capable of hybridizing with probes 1, 2 and 3 of pHTA2 shown in FIG. 2. The fragment of 3 kb corresponds more particularly to the restriction fragment HindIII-PstI.

The sequences of nucleotides of the invention are, in addition, characterized in that they contain sites in the following order: HindIII-HincII-BglII-KpnI-HindIII-PstI.

In a preferred manner, these sequences of nucleotides are obtained by in vitro genetic recombination of DNA sequences derived from at least one strain of *B.thuringiensis*. In a variant of the embodiment of the invention, two different strains of *B.thuringiensis* are utilized.

Strains of *B.thuringiensis* particularly suited for obtaining these sequences of nucleotides are the strains corresponding to *aizawai* 7-29 and *entomocidus* 6-01, deposited on Apr. 21, 1987 under the No. I-661 and No. I-660, respectively, with the National Collection of Cultures of Microorganisms (N.C.C.M.) in Paris.

In an advantageous manner, the sequences of nucleotides of the invention code, for a polypeptide capable of forming an immunological complex with antibodies directed against polypeptides showing the larvicidal activity with regard to *S.littoralis*.

DETAILED DESCRIPTION OF THE INVENTION

A sequence of nucleotides according to the invention is characterized in that it has the capacity to hybridize with a probe formed from the sequence (I) showing the following chain arrangement (nucleotides 52–990 of SEQ ID NO:1):

```
      52
GTC   TAC   TTG   ACA   GGG   GTA   GGA   ACA   TAA   TCG   GTC   AAT   TTT   AAA
                                          112
TAT   GGG   GCA   TAT   ATT   GAT   ATT   TTA   TAA   AAT   TTG   TTA   CGT   TTT
                                                                              172
TTG   TAT   TTT   TTC   ATA   AGA   TGT   GTC   ATA   TGT   ATT   AAA   TCG   TGG

TAA   TGA   AAA   ACA   GTA   TCA   AAC   TAT   CAG   AAC   TTT   GGT   AGT   TTA
                              232
ATA   AAA   AAA   CGG   AGG   TAT   TTT   ATG   GAG   GAA   AAT   AAT   CAA   AAT
                                                                  292
CAA   TGC   ATA   CCT   TAC   AAT   TGT   TTA   AGT   AAT   CCT   GAA   GAA   GTA

CTT   TTG   GAT   GGA   GAA   CGG   ATA   TCA   ACT   GGT   AAT   TCA   TCA   ATT
                  352
GAT   ATT   TCT   CTG   TCA   CTT   GTT   CAG   TTT   CTG   GTA   TCT   AAC   TTT
                                                      412
GTA   CCA   GGG   GGA   GGA   TTT   TTA   GTT   GGA   TTA   ATA   GAT   TTT   GTA

TGG   GGA   ATA   GTT   GGC   CCT   TCT   CAA   TGG   GAT   GCA   TTT   CTA   GTA
      472
CAA   ATT   GAA   CAA   TTA   ATT   AAT   GAA   AGA   ATA   GCT   GAA   TTT   GCT
                                          532
AGG   AAT   GCT   GCT   ATT   GCT   AAT   TTA   GAA   GGA   TTA   GGA   AAC   AAT
                                                                              592
TTC   AAT   ATA   TAT   GTG   GAA   GCA   TTT   AAA   GAA   TGG   GAA   GAA   GAT

CCT   AAT   AAT   CCA   GAA   ACC   AGG   ACC   AGA   GTA   ATT   GAT   CGC   TTT
                              652
CGT   ATA   CTT   GAT   GGG   CTA   CTT   GAA   AGG   GAC   ATT   CCT   TCG   TTT
                                                                  712
CGA   ATT   TCT   GGA   TTT   GAA   GTA   CCC   CTT   TTA   TCC   GTT   TAT   GCT

CAA   GCG   GCC   AAT   CTG   CAT   CTA   GCT   ATA   TTA   AGA   GAT   TCT   GTA
                  772
ATT   TTT   GGA   GAA   AGA   TGG   GGA   TTG   ACA   ACG   ATA   AAT   GTC   AAT
                                                      832
GAA   AAC   TAT   AAT   AGA   CTA   ATT   AGG   CAT   ATT   GAT   GAA   TAT   GCT

GAT   CAC   TGT   GCA   AAT   ACG   TAT   AAT   CGG   GGA   TTA   AAT   AAT   TTA
      892
CCG   AAA   TCT   ACG   TAT   CAA   GAT   TGG   ATA   ACA   TAT   AAT   CGA   TTA
                                          952
CGG   AGA   GAC   TTA   ACA   TTG   ACT   GTA   TTA   GAT   ATC   GCC   GCT   TTC

TTT   CCA   AAC   TAT   GAC
```

Sequences of nucleotides coding for at least a part of the N-terminal region of a polypeptide toxic specifically towards larvae of Lepidoptera of the Noctuidae family, and preferably towards *S.littoralis*, are characterized in that they contain the chain arrangement (I) defined above.

In an advantageous manner, the sequence of nucleotides characterized by the chain arrangement defined above codes for a part of a polypeptide having a higher larvicidal activity towards *S.littoralis* than that of the polypeptides encoded by natural isolates presently known for their effects against *S.littoralis.*

The study of this sequence of nucleotides shows that it is characterized by an initiation codon ATG situated at position 241 starting from which an open reading frame of 750 nucleotides has been identified.

This sequence is also characterized by a GGAGG attachment site for ribosomes at positions 230 to 234.

According to another feature, the sequence of nucleotides of the invention is characterized in that it contains, upstream from the ATG codon, a sequence going from the nucleotide at position 137 to the nucleotide at position 177, strongly homologous with the region found by Wong et al. (1983) and described in (16) upstream from the gene for the crystal of the strain *kurstaki* HD1 Dipel (BTK) and for which the authors have shown that it contains three promoters BtI, BtII and Ec which are functional in *B.thuringiensis* and *E.coli*, respectively. The homology of these sequences is about 70%.

The invention also relates to a sequence of nucleotides coding for the following sequence (II) of amino acids (amino acids 1–250 SEQ ID NO:2):

```
                                        MET GLU GLU ASN ASN GLN ASN
GLN CYS ILE PRO TYR ASN CYS LEU SER ASN PRO GLU GLU VAL
LEU LEU ASP GLY GLU ARG ILE SER THR GLY ASN SER SER ILE
ASP ILE SER LEU SER LEU VAL GLN PHE LEU VAL SER ASN PHE
VAL PRO GLY GLY PHE LEU VAL GLY LEU ILE ASP PHE VAL TRP
GLY ILE VAL GLY PRO SER GLN TRP ASP ALA PHE LEU VAL GLN
ILE GLU GLN LEU ILE ASN GLU ARG ILE ALA GLU PHE ALA ARG
ASN ALA ALA ILE ALA ASN LEU GLU GLY LEU GLY ASN ASN PHE
ASN ILE TYR VAL GLU ALA PHE LYS GLU TRP GLU GLU ASP PRO
ASN ASN PRO GLU THR ARG THR ARG VAL ILE ASP PRG PHE ARG
ILE LEU ASP GLY LEU LEU GLU ARG ASP ILE PRO SER PHE ARG
ILE SER GLY PHE GLU VAL PRO LEU LEU SER VAL TYR ALA GLN
ALA ALA ASN LEU HIS LEU ALA ILE LEU ARG ASP SER VAL ILE
PHE GLY GLU ARG TRP GLY LEU THR THR ILE ASN VAL ASN GLU
ASN TYR ASN ARG LEU ILE ARG HIS ILE ASP GLU TYR ALA ASP
HIS CYS ALA ASN THR TYR ASN ARG GLY LEU ASN ASN LEU PRO
LYS SER THR TYR GLN ASP TRP ILE THR TYR ASN ARG LEU ARG
ARG ASP LEU THR LEU THR VAL LEU ASP ILE ALA ALA PHE PHE
PRO ASN TYR ASP
```

A better identification of the sequence of nucleotides isolated from the above strains, deposited with the NCCM has made it possible to observe that the nucleotide situated at position 273 is guanine (G), the amino acid resulting from the GTA codon thus being valine.

Now, the reading of the nucleotide corresponding to this position 273 in the application FR.8708090 of Jun. 10, 1987 had led to reporting thymine (T) and leucine as amino acid resulting from the TTA codon.

Another sequence of nucleotides of the invention is characterized by its capacity of hybridization with a probe formed from the sequence (III) showing the following chain arrangement (SEQ ID NO:1):

```
   1 AAG CTT CAA TAG AAT CTC AAA TCT CGA TGA CTG CTT AGT CTT TTT AAT ACT GTC TAC TTG ACA GGG GTA ACA TAA TCG GTC AAT TTT
  91 AAA TAT GGG GCA GTA TAT ATT GAT TAT AAT ATT CAG CCT GAA TTT TAA TTT TTT CGT TTA TTG AGT CTT CGT ATA AGA TGT GAG ATA TCG AAA TGG TAA
 181 TGA ACA GTA TCA AAC ATT AAC AAC TTA GGT GTA CCA CAA TTA GCA CAA ATT TAT CAA CAA TGT AAT ATT CAA TTT TAT TCA
 271 CCT TAC AAT TGT TTT AGT CTG GTA CTA AAT GAT CAT TAT AAT GAA TTT GAA TTT GTA CTT ATA GCT ATT AAT GAT GTG CTT TCA TCA
 361 CTT GTT CAG TTT GCA AAC AAT CTA TTC AAT GAT CAT AGG ACA CAG ACT TTT GGA GTT AAT GCT ATA TCA TTA GAA
 451 CAA TGG GAT GCA AAT ATT GAT GTA AAT GGG CTA ATA CTT CTG GGG TTA AGA CAG TTA AAT ATT AAG GCT ATT AAT
 541 GGA TTA GGA AAC CGT ATA AAT ATT ACT CTT CTA TTC GAT CAT AGG ACA CAG ACT TTT GGA GTT AAT GCT ATA TCA TTA GAA
 631 GAT TGG GAT GCC GCC AAT GAT GTA GCT CTG ATT ATA AAT CAT TAT ATA CCA AAC GCT ACC CCC ACG TTA GTT TAT
 721 GCT CAA AGA TAT CGT ATA GCG GTT GTT AAT ATT TCT CGA ATT TGT ACA GTT AGA CGA TTT GGT GAT AAA TCC GTC AAA
 811 AAC TAT AAT AGA GAG AAC CAT AGG ACA CAG ACT GCT AGA TAT CGG CTA TTA CCA TAT TTA AAT AAT TTC AAT AAT TTA
 901 ACG TAT CAA GAT GGT TGC CCT CAA CAC GAT GAC AGG AGC ACA GTT AGA CGA TTT GGT GAT AAA TCC GTC AAA
 991 AAT AGG AGA CTA TTA CCA ATG GAG TAT TTT CCT CAT ACT TGG AGA TCC AAT TTA CCT AAC TTA ACA ATA CCT AGC CAT ACT TTT
1081 GTA GCT CAA ACT CCT TTA AAC CGC CAG CGC TGC CAG CGC CAC TCT GAT GAG ACT GGT GAG ACT TCT CCT ACG ACT CTT CGT
1171 ACG GAT TGG TTT AGT GTT GGA AAC CGG TGC CAG CAC TTA ACT TGT ACA CCT ATA GGA GAA TAT ATT AGC CAT ACT TTT
1261 ATA TAT CAA AGA GAT TGG CCA TTT AAT CGC CAG CGC GAT GTT TGG GAT ATA GGA GAA GGA GAT GAA AAT GTA TTT ACG CTT
1351 TTA CAA AGA CAA CCT AGT CAA AAC CAG CAG CGC TCT GAT TTA AAT TCA AGG CCT GAA CCA CGT AGT TGT AAT ACG TTA
1441 CGA AGA AGA ACG CCT GAT GTT CAA GAT GAT TCT CGG CCG ACG CAC ACT AGC AGT AGT GTT TGT CTT TTA ACG TGT
1531 CAT GCA ACT TTT GTT CAA AGA CTA ACA TCT GGA TCT TTA ACA CCT ACA AAT ACA GAC TAT AAT
```

-continued

| 1621 ACA | ATT | GAT | CCA | GAG | AGA | ATT | AAT | CAA | ATA | CCT | TTA | GTG | AAA | GGA | TTT | AGA | GTT | TGG | GGG | GGC | ACC | TCT | GTC | ATT | ACA | GGA | CCA | TTT |
| --- | --- | --- | --- | --- | --- | --- | --- | --- | --- | --- | --- | --- | --- | --- | --- | --- | --- | --- | --- | --- | --- | --- | --- | --- | --- | --- | --- | --- |
| 1711 ACA | GGA | GGG | GAT | ATC | CTT | CGA | AGA | AAT | ACC | TTT | GGT | GAT | TTT | GTA | TCT | CTA | CAA | AAT | ATT | AAT | TCA | CCA | AGA | GTT | TTT | TAC | CGT |
| 1801 TTA | AGA | TTT | CGT | TAC | GCT | TCC | AGT | AGG | ATA | AGT | CGA | GAT | GTT | ATA | TTA | ACA | GGA | ACA | GCG | TCC | ACA | ACC | GGC | CAA | AGA | GTT | CAA | GTA |
| 1891 GAT | ATG | CCT | CTT | CAG | AAA | ACT | ATT | GAA | GGG | GAA | ATA | AGT | ATG | GAA | ACA | TCT | AGA | GTT | ACA | TTT | CCT | AAT | ATA | GAT | TTT | TCA | TTT |
| 1981 AGA | GCT | AAT | CCA | GAT | ATA | CTA | GCA | ATA | TTT | ACG | GTC | GAA | CAA | CCT | CTA | TTT | GGT | GCA | AGA | GTT | GAA | CTT | AGT | GAT | ATA | TCT | AAA | ATT |
| 2071 GAG | ATT | ATT | CTA | GAT | ACC | ATA | GCA | GTG | ACA | ACA | AGT | AGC | GTG | GCA | AAG | TTA | ATT | AAG | AGC | CTG | ACT | TCT | TCC | AAT |
| 2161 CAA | ATC | GGG | TTA | AAA | CCA | GAA | TTG | TCC | CGT | GGC | CGT | TGG | GAG | CGT | TGT | CTT | TCC | ACC | CAG | AAT | TTC | TTA | CAA | GAG | CCA | TTT | CTG | GAT |
| 2251 GAA | AAG | CGA | GAA | CCA | GAC | GAC | CGT | GGC | TGG | AGA | GGA | TCG | AAA | GAT | GAT | TTA | ACC | GTA | GCT | AAA | TAC | CGT | TAT | GTC | AGA | ACA |
| 2341 AAT | AGA | CAA | ATA | ATA | ATC | ACC | ATT | CAG | ATC | GCG | TAC | AAT | CGT | CCA | AAT | TAT | AGA | TTA |
| 2431 CCG | GGT | ACC | GTT | GAT | GAT | AGT | GAA | GAT | TAT | TAT | TTG | AAG | TGT | GGA | GAA | AAA | CAC | GAA | ATA | GTA | CTT | CCA | GGC | ACG | GGT | CTA | AGA |
| 2521 GGG | TAT | ATC | GAA | GAT | AGT | TCA | GCC | CAA | GAC | TTA | GAA | ATC | GGA | AAT | ATC | GCG | CGA | GAA | AAT | CAC | CCA | GCG | GAA | AAT | GTG | TGG | CCT | CTA |
| 2611 TTA | TGG | CCG | CTT | TCA | GCC | CAA | AGT | AAG | TGT | | | | | | | | | | | | | | | | | | | |
| 2701 TGT | TCC | TGC | AG | | | | | | | | | | | | | | | | | | | | | | | | | |

In a distinctive manner, sequences of nucleotides of the invention coding for a polypeptide toxic specifically towards larvae of Lepidoptera of the Noctuidae family, and preferably toward *S.littoralis* comprise or are constituted by the chain arrangement (III) previously defined.

The chain arrangement (III), comprised in the sequence of nucleotides of the invention contains 2711 nucleotides. This fragment includes in particular the potential promoter of the gene of the δ-endotoxin active on *S.littoralis*.

Sequences of nucleotides modified in relation to the chain arrangements (I) or (III) described above naturally enter into the framework of the present invention to the extent to which these modifications do not generate appreciable variations of the toxicity of the polypeptide coded by the modified sequence towards *S.littoralis*.

These modifications may, for example, consist of deletions, substitutions, recombinations.

Thus, the sequences of nucleotides (I) and (III) contain at their position 611 a variable nucleotide corresponding to adenine (A) in the sequence (I) and to cytosine (C) in the sequence (III). These nucleotides enter into the composition of the respective codons GAA and GCA which code respectively for the amino acids glutamic acid (GLU) and alanine (ALA) in the respective sequences II and IV.

Similarly, any sequence of nucleotides which can hybridize with that of the chain arrangements (I) or (III) such as obtained by reverse enzymatic transformation of the corresponding RNA or even by chemical synthesis also enter into the framework of the definitions of the invention.

The sequence of nucleotides of formula (III) starts with a ATG initiation codon situated at position 241 and which represents the start of an open reading frame of 2470 nucleotides.

The invention also relates to a sequence of nucleotides characterized in that it codes for a polypeptide containing the sequence (IV) of amino acids below (SEQ ID NO:2):

```
 271  PRO TYR ASN CYS LEU SER ASN PRO GLU VAL LEU LEU ASP GLY PHE GLU ARG ILE SER THR MET GLU ASN ASN GLN ASN GLN CYS ILE
 361  LEU VAL GLN LEU PHE SER ASN PRO ASN PHE VAL LEU GLY LEU PHE ILE SER THR GLY ASP SER ASN SER ILE SER LEU PRO SER LEU
 451  GLN TRP ASP ALA PHE LEU VAL SER ASN PHE VAL PRO GLY ARG LEU ILE ILE TRP ASP ALA ALA VAL GLY ALA ALA ILE VAL GLY LEU
 541  GLY LEU GLY ASN PHE ASN VAL GLN ILE ASP GLY PHE ARG ALA GLU ASP PRO ASN ALA ASN THR ALA LEU LEU SER ARG VAL ASN LEU
 631  ASP ARG PHE ARG ILE LEU ASP LYS ILE TYR ALA PHE GLU TRP GLU ASP SER ILE PRO SER GLY PHE ARG LEU SER VAL ARG LEU GLU
 721  ALA GLN ALA ALA ASN LEU HIS LEU ALA ILE ARG ARG ARG LEU PHE GLY ILE ASP ARG LEU ARG THR LEU ASN ASN ASN VAL LYS GLU
 811  ASN TYR ASN ARG LEU ILE ARG ASP ALA HIS TYR ALA THR GLU ARG ASN ARG TYR VAL ASN ALA LEU ASN ASN LYS LYS SER ASN ILE
 901  THR ASP TRP ASP TRP ILE THR ILE CYS LEU LEU THR VAL GHR ASP HIS PRO THR ILE PRO LEU GLN LEU ILE GLY GLN LEU PRO ASN
 991  ASN ARG GLN LEU PRO THR GLN PHE ASN ARG GLU GLY ASN TYR ASP ARG ALA PRO HIS LEU ASP ARG ILE LEU SER ILE ASN GLN SER
1081  VAL ALA GLN ILE LEU SER VAL ARG GLY TYR MET TYR ASN ILE GLY HIS HIS LEU LEU SER TRP ILE GLY LEU VAL LEU GLN THR LEU
1171  THR ASP TRP PHE PHE ARG GLU ALA PHE PRO ARG TYR HIS ARG PHE GLN GLY SER PHE PHE THR TRP PRO TYR ASN ILE SER THR LEU
1261  ILE TYR GLY ARG GLU SER ASN GLN ASN ARG LEU ILE ARG PRO THR ARG GLY GLU ASP PRO ARG THR SER GLY THR ILE ILE THR LEU
1351  LEU LEU GLN LEU VAL GLN SER CYS ARG ASN ARG ARG HIS PHE ARG GLY LEU LEU ALA SER ARG VAL SER SER PHE ALA HIS SER TYR
1441  ARG GLY ARG GLY THR ARG VAL ASP LYS ASP THR PRO HIS LEU LEU PRO THR LEU PHE ARG HIS PHE ALA THR ILE LEU THR LEU CYS
1531  HIS ALA THR PHE PHE VAL LYS GLU LEU THR LEU GLU THR ARG ARG SER GLU VAL HIS SER ARG VAL ILE PHE HIS THR THR LEU ASN
1621  THR ILE ASP PRO GLU GLN GLY PHE VAL PHE LEU GLY VAL LEU PRO ARG GLY PHE GLY TRP TRP SER ILE THR GLY GLY ARG PRO PHE
1711  THR GLY ASP ILE LEU ARG ASN ARG VAL LEU GLY PHE SER VAL GLN VAL ASN ILE THR GLN GLN THR GLN GLN ARG LEU ARG TYR ARG
```

-continued

| | | | | | | | | | | | | | | |
|---|---|---|---|---|---|---|---|---|---|---|---|---|---|---|
| 1801 LEU | ARG | PHE | ARG | TYR | ALA | SER | ARG | ASP | ALA | ARG | VAL | ILE | VAL | LEU | THR | GLY | ALA | ALA | SER | THR | GLY | VAL | GLY | GLN | VAL | SER | VAL |
| 1891 ASN | MET | PRO | LEU | GLN | LYS | THR | MET | GLU | ILE | GLY | ASN | LEU | SER | ARG | TYR | THR | ASP | PHE | SER | ASN | PRO | PHE | SER | PHE |
| 1981 ARG | ALA | ASN | PRO | ASP | ILE | LYS | THR | ILE | GLY | ILE | SER | PRO | LEU | PHE | GLY | ALA | ARG | ILE | SER | GLY | GLU | LEU | ILE | ASP | TYR | ILE | LYS |
| 2071 GLU | ILE | ILE | LEU | ALA | ASP | ALA | ASP | PHE | GLU | ALA | GLU | ALA | ARG | GLN | LEU | SER | GLY | VAL | ASN | ALA | LEU | PHE | THR | ILE | ASP | SER | ASN |
| 2161 GLN | ILE | LEU | LYS | THR | ASP | VAL | HIS | TYR | GLN | LEU | VAL | SER | ILE | ALA | CYS | LEU | ASP | GLU | PHE | CYS | LEU | SER |
| 2251 GLU | LYS | ARG | GLU | LEU | SER | GLU | LYS | VAL | HIS | ALA | ARG | LEU | ARG | ASN | LEU | GLN | ASP | PRO | ASN | PHE | ARG | GLY | ILE |
| 2341 ASN | ARG | GLN | PRO | ASP | ARG | GLY | TRP | ARG | GLY | SER | THR | LEU | TYR | ILE | GLN | ASP | LYS | PHE | LYS | GLU | ASN | TYR | VAL | THR | LEU |
| 2431 PRO | GLY | THR | VAL | ASP | CYS | TYR | PRO | THR | LEU | TYR | GLN | ILE | ILE | ASP | SER | LYS | ALA | TYR | THR | ARG | TYR | GLU | LEU | ARG |
| 2521 GLY | TYR | ILE | GLU | ASP | SER | GLN | ASP | LEU | GLU | ILE | TYR | LEU | ILE | ALA | LYS | HIS | GLU | ILE | ASN | VAL | PRO | GLY | THR | GLY | SER |
| 2611 LEU | TRP | PRO | LEU | SER | ALA | GLN | SER | PRO | ILE | GLY | LYS | CYS | GLY | GLU | PRO | ASN | ARG | CYS | ALA | PRO | HIS | LEU | GLU | TRP | ASN | PRO | ASP | LEU | ASP |
| 2701 CYS | SER | CYS |

The invention also relates to recombinant expression and cloning vectors comprising more particularly at least one sequence of nucleotides such as that defined above, in particular at least a part of the sequence of about 3 kb.

A specific recombinant vector is, for example, a plasmid containing the HindIII-PstI fragment of the sequence of nucleotides of the invention, inserted in a vector pUC9. A first preferred vector is the plasmid pHT71, the construction of which is reported in the assemblies below, which comprises a HindIII-PstI DNA fragment according to the invention constituted uniquely of DNA derived from the strain *aizawai* 7-29.

Another recombinant vector is constituted by the plasmid pHT 671, the construction of which is given in FIG. 4. This plasmid contains a chimeric HindIII-PstI fragment, obtained by fusing a HindIII-HindII fragment of 1.1 kb derived from the strain *entomocidus* 6-01 with a HincII-PstI fragment of 1.9 kb derived from the strain *aizawai* 7-29.

The modified bacterial strains which contain one of the nucleotide sequences defined above or also a recombinant expression vector and cloning previously defined, and preferably the plasmid pHT671 or the plasmid pHT71, also enter into the framework of the invention.

The invention also relates to a polypeptide toxic towards larvae of Lepidoptera and in a preferential manner towards *S.littoralis*, which attack cotton leaves or other crops such as those listed above, characterized in that it is capable of forming an immunological complex with antibodies directed against polypeptides with larvicidal activity towards *S.littoralis.*

The invention relates more particularly to the $NH_2$-terminal part of this polypeptide which contains the larvicidal activity.

The extremity of the active $NH_2$-terminal part corresponds to the sequence (II) of amino acids given above.

A preferred polypeptide of the invention is that which corresponds to this sequence (II) and corresponds to the sequence (IV) of amino acids given in the preceding pages. This polypeptide corresponding to the sequence (IV) contains 823 amino acids. Its calculated molecular mass is 92906 Da.

This sequence of δ-endotoxin was compared with amino acid sequences of δ-endotoxins derived from other strains of *B.thuringiensis* active on the Lepidoptera and the genes of which have been isolated and sequenced previously: the δ-endotoxins in question are those of the strains *kurstaki* HD1 (19), *kurstaki* HD73 (20), *berliner* 1715 (21) and (22) *Sotto* (23) and *aizawai* IPL7 (24).

The results of these comparisons indicate that all are different in the second quarter of the molecule (amino acids 281 to 620) whereas the $NH_2$-terminal part (amino acids 1 to 280) and the COOH-terminal domain (amino acids 621 to 1175) of the protein are highly conserved and differ only by several amino acids. On the other hand, the δ-endotoxin corresponding to the sequence (IV) above shows considerable differences from the other δ-endotoxins both in the $NH_2$-terminal part (amino acids 1 to 280) and in the second quarter of the molecule (amino acids 281 to 620). The results of these comparisons indicate again that the $NH_2$-terminal half of the molecule (amino acids 1 to 620) which corresponds to the toxic fraction of the protein only show 46% homology with the other δ-endotoxins. The most important differences are located in the second half of the toxic part of the molecule (amino acids 281 to 620) with only 36% of identical amino acids, the $NH_2$-terminal part (amino acids 1 to 280) itself showing 58% of amino acids identical with the other δ-endotoxins. Such considerable differences have never been observed up to now in the $NH_2$ terminal part of the toxic fraction of the molecule among the δ-endotoxins active on the Lepidoptera.

In order to obtain a sequence of nucleotides entering into the framework of the invention, coding for at least the active part of a polypeptide showing a specific toxicity towards larvae of Lepidoptera of the Noctuidae family, and preferably towards *S.littoralis*, recourse is had, in conformity with the invention, to the following steps, namely:

the carrying out of a molecular hybridization between, on the one hand, a nucleotide sequence of a strain of *B.thuringiensis* active against *S.littoralis* and, on the other, at least two nucleotide sequences, used as probes, derived from the 5' part of a restriction fragment of a gene for δ-endotoxin of *B.thuringiensis*, this part coding for the $NH_2$-terminal part of the polypeptide active on the larvae of Lepidoptera, and from the 3' part of this fragment coding for the COOH part of the polypeptide, the isolation of the hybrid fragment, its cloning in a vector, followed by its purification.

In an advantageous manner, the hybridization probes utilized are obtained from a gene for the δ-endotoxin derived from the strain *aizawai* 7-29 coding for a protein of 130 kDa, active against *P.brassicae* and inactive towards *S.littoralis*, this gene having been cloned in the recombinant plasmid pHTA2.

In an embodiment of the preceding procedure, the fragment recombined with the vector in the cloning step is elaborated from a HindIII-PstI restriction fragment derived from a single strain of *B.thuringiensis*, preferably *aizawai* 7-29. In particular, this fragment is carried preferentially by the recombinant plasmid pHTA6 such as isolated with the aid of a probe constituted by a PvuII fragment of 2 kb of the plasmid pBT15–88 corresponding to the internal part of a gene for the chromosomal crystal of the strain *berliner* 1715, starting from transforming clones containing nucleotide sequences derived from *B.thuringiensis* strains active against larvae of Lepidoptera, inter-alia of *S.littoralis.*

In another embodiment of the invention, the fragment recombined with the vector in the cloning step is elaborated from several sequences of nucleotides derived from recombinant vectors containing sequences of nucleotides from at least two different strains of *B.thuringiensis*, possessing the same restriction maps and themselves containing all or part of the sequences of nucleotides capable of coding for a polypeptide active, in a preferential manner, against *S.littoralis.*

In this case, the recombined fragment used in the cloning step is a fragment of about 3 kb, advantageously elaborated from a HindIII-HincII restriction fragment of about 1.1 kb derived from the *entomocidus* 6-01 strain and a HincII-PstI fragment of about 1.9 kb from the *aizawai* 7-29 strain. It corresponds to a truncated gene for δ-endotoxin.

The HindIII-HincII and HincII-PstI restriction fragments are carried more especially by the respective recombinant plasmids pHTE6 and pHTA6 such as isolated with the aid of the probe constituted by the PvuII fragment mentioned above.

The study of the toxicity towards the larvae of Lepidoptera of the bacterial strains modified with the aid of the sequences of nucleotides defined above, has made it possible to demonstrate their high toxic activity, in particular with regard to the caterpillars of *S.littoralis*.

This activity was estimated from the point of view of the specificity index corresponding to the ratio LC50 *S.littoralis*/LC50 *P.brassicae* in which "LC50" represents the lethal concentration killing 50% of the larvae in 72 hours.

The utilization of such an index makes it possible to evaluate the activity of the bacterial strains studied without having to consider the level of expression of the polypeptides.

The results obtained, which are reported in the examples which follow, and the values of LD50 which are deduced from them, have shown that the bacterial strains modified according to the invention show a more specific toxic activity towards *S.littoralis* than the native crystal proteins of the strains *aizawai* 7-29 or *berliner* 1715.

Therefore, the invention relates to the use of these modified strains, of recombinant vectors containing the nucleotide sequences defined above, in particular the plasmid pHT671 and the plasmid pHT71, and these sequences themselves for the elaboration of larvicidal compositions preferentially toxic towards *S.littoralis*.

The larvicidal compositions of the invention are thus characterized in that they contain an efficaceous quantity of polypeptides such as defined above or expressed by the nucleotide sequences mentioned above.

In order to produce these polypeptides the truncated genes for δ-endotoxin corresponding to the nucleotide sequences of the invention are advantageously implemented.

These genes can be used to produce in excess the toxic polypeptide in microorganisms permitting the expression of the above recombinant vectors. Suitable strains of microorganisms include *E.coli* or also *B.subtilis*.

These truncated genes may be reintroduced into the strains of *B.thuringiensis* or into related species such as *B.cereus*, according to the standard techniques, for example, by transformation, conjugation or transduction. These techniques make it possible to produce the toxic polypeptide in large quantity without first having to modify the natural region of the promoter for the δ-endotoxin genes of *B.thuringiensis*.

This transformation may be carried out by using methods derived from the transformation of the protoplasts of *B.subtilis* according to (11) or of the vegetative cells of *B.thuringiensis* as described in (12).

The introduction of recombinant plasmids by a system of the conjugation type may be carried out by using *B.thuringiensis* as host strain and *B.subtilis* or *Streptococcus faecalis* as strains of the donor type by operating according to (13) and (14).

As a variant, the sequences of nucleotides are introduced into microorganisms living in the environment or in association with the plants and capable of expressing recombinant vectors containing these sequences. The introduction may be carried out in microorganisms such as Pseudomonas by working according to the procedure described in (17), by the intermediary of plasmid vectors containing the transposon Tn5 and the gene for the toxin, or Azospirillum or Rhizobium by means of the intermediary of suicide vectors derived from the plasmid RP4 and of mobilizing plasmids functional in Gram negative bacteria (for example, pRK2013) according to the procedures described in (18).

The truncated genes are alone in the strains of Bacilli or, as a variant, are associated with different δ-endotoxin genes which makes it possible to obtain crystals synthesized by these strains specifically toxic towards given species of Noctuidae, or toxic both towards the Noctuidae and insects sensitive to other δ-endotoxins. These recombinations, carried out in vitro or in vivo with the nucleotide sequences of the invention and other δ-endotoxin genes showing different toxic specificities, lead to the construction of new genes coding for novel hybrid toxic proteins exhibiting a large spectrum of activity towards insects. These new genes and these novel proteins also enter into the framework of the invention.

In these applications, the nucleotide sequences of the invention may be transferred and expressed in plants sensitive to *S.littoralis* in order to diminish the devastation caused by these insects.

Among the plants to be protected, mention should be made of: cotton, clover, the tomatoe and alfalfa.

The transfer of the truncated gene into cotton plants may be carried out by transformation involving strains such as Agrobacterium as described in (15).

In addition, the invention relates to the plant cells, the plants and the seeds containing the nucleotide sequences defined above.

The plant cells according to the invention are cells, the genome of which after transformation by a non-essentially biological procedure possesses in a stable manner a sequence of nucleotides capable of expressing a polypeptide toxic towards *S.littoralis*, such as that defined above. The invention also relates to the plant cells derived from their division.

The plants according to the invention are plants transformed by a non-essentially biological procedure, having in particular as predator *S.littoralis*, the genome of which possesses in a stable manner a sequence of nucleotides such as that defined above, capable of expressing a polypeptide toxic towards *S.littoralis*. The plants in question are also plants derived from their reproduction, their multiplication or hybrid crosses.

In accordance with another feature, the invention relates to plants having in particular as predator *S.littoralis*, possessing in addition to their initial phenotypic and genotypic characters the property of expressing a polypeptide toxic preferentially towards *S.littoralis*, this property resulting from the insertion in their genome by means of genetic manipulation of a sequence of nucleotides capable of expressing the said polypeptide.

In addition, the invention relates to seeds capable of giving rise to a plant such as that defined above or derived from such a plant, characterized in that they have integrated into their genome by genetic manipulation a nucleotide sequence described above.

BRIEF DESCRIPTION OF THE DRAWINGS

Other characteristics and advantages of the invention will become apparent in the course of the description and in referring to the examples.

FIG. 5 shows the photographs of the immunodiffusion tests. In FIGS. 5A and 5B, solubilized, purified crystal of *aizawai* 7-29 was placed in well No. 1 to serve as a positive control and wells No. 2, 3, 4, 5, and 6 contained *E. coli* clones containing the plasmids pHT671, pHTA4, pHTA2, pHT71 and pUC18, respectively.

EXAMPLE 1

Construction of a DNA Sequence of About 3 kb Containing a Hybrid Gene of an Insecticidal Toxin This construction comprises:

1/ the preparation of gene banks of *B.thuringiensis*

2/ the selection and characterization of transforming clones containing the genes of a crystal protein and nucleotide sequences responsible for the larvicidal activity, 3/ in vitro recombination of these sequences in a cloning vector with construction of the plasmid pHT671.

These different steps are carried out as follows:

1/ Preparation of Gene Banks of *B.thuringiensis*

The total DNA of the *aizawai* 7-29 and *entomocidus* 6-01 strains of *Bacillus thuringiensis* is purified by using the method reported in (1) and 50 μg of each purified DNA are completely digested with the restriction enzyme PstI.

The DNA digested by PstI is analysed by horizontal electro-phoresis on a 0.8% agarose gel and DNA fragments of a size of 5 to 8 kb are recovered from the agarose gels by electroelution in a manner described in (2).

The purified DNA fragments of 5–8 kb of the *aizawai* 7-29 strain are ligated to the DNA of the cloning vector pUC18 digested by PstI according to (3).

The purified DNA fragments of 5–8 kb of the *entomocidus* 6-01 chain are ligated to the DNA of the cloning vector pUC9 digested by PtI. The cells of *E.coli* JM83 are transformed with the ligation mixture as described in (4).

The transforming clones of *E.coli* are selected on LB medium containing 100 μg/ml of ampicillin.

2/ Isolation and Characterization of the Transforming Clones Containing the Genes for a Crystal Protein A/ Screening of the transformed *E.coli* cells with the aid of an internal fragment of a gene of the crystal protein labelled with $^{32}P$, used as probe:

Transforming clones containing recombinant plasmids carrying the gene for the crystal are detected by colony hybridization according to the method described in (5), by using as probe a PvuII fragment of 2 kb of the pBT 15-88 plasmid corresponding to an internal part of the gene for the crystal protein located on the chromosome of the *berliner* 1715 strain.

B/ Characterization of the recombinant plasmids present in the clones which react with the above probe.

Two recombinant plasmids, pHTA6 and pHTE6, isolated respectively from gene banks constructed from the strains *aizawai* 7-29 and *entomocidus* 6-01, show a homology with this probe. In each case, a DNA fragment of about 6.6 kb was cloned.

The restriction map of the two plasmids is given in FIG. 1. The comparison of the restriction sites shows that the two DNA fragments cloned appear to be identical.

In order to delimit the sequences corresponding to the gene for the δ-endotoxin, different DNA fragments labelled with $^{32}P$, derived from a gene of the crystal previously characterized, and cloned in the recombinant plasmid pHTA2, are utilized as probes. This latter gene for the crystal also derived from the *aizawai* 7-29 strain codes for a protein of 130 kd active against *P.brassicae* but not against *S.littoralis*. This type of gene possesses the same restriction map as the gene for the δ-endotoxin derived from the *berliner* 1715 strain. In FIG. 2 is shown the restriction map of this gene for the crystal protein of the *aizawai* 7-29 strain cloned in the plasmid pHTA2. The thick lines shown above the map correspond to the fragments used as hybridization probes.

The plasmids pHTA6 and pHTE6 are hydrolysed by different restriction endonucleases, analysed by horizontal electrophoresis on a 0.8% agarose gel and hybridized with the different probes.

The transfer of the DNA to nitrocellulose filters is carried out according to the method of SOUTHERN described in (6). The hybridization is conducted at 42° C. for 24 hours in a solution containing: 5×SSC, 30% formamide and a 1×Denhardt mixture described in (7) in the presence of a DNA probe labelled with $^{32}P$. The filters are then washed at 42° C. for 20 minutes, by using successively the following solutions: 5 SSC in 50% formamide, 5 SSC, 2 SSC, 1 SSC and 0.5 SSC before being dried at room temperature.

The results of these hybridization experiments are summarized in FIG. 3. It appears that each extremity of the cloned DNA fragments of 6.6 kb shows a homology with the probes. The PstI-KpnI fragment of 1.5 kb reacting with the probe No. 3 corresponds to the 3' end of a gene of the crystal protein present in both the *aizawai* 7-29 and *entomocidus* 6-01 strains. As pointed out in FIG. 3, the probes No. 1 and No. 2 corresponding to the 5' end of the gene for the δ-endotoxin of pHTA2 hybridize with the HindIII-HincII fragment of 1.1 kb contained in the plasmid pHTA6. The probe No. 3 which covers the 3' end of the gene of the δ-endotoxin of pHTA2 hybridizes with the HindIII-PstI fragment of 0.4 kb contained in the plasmid pHTA6. It should be noted that a weak hybridization signal is obtained with the probe No. 2 whereas the two other probes give easily detectable signals.

From these results, the inventors have established that the HindIII-PstI DNA fragment of 3 kb corresponds to a large part of a gene for the δ-endotoxin which commences close to the central HindIII site. It seems clear in the light of results of the hybridization experiments that the gene for the δ-endotoxin shows substantial differences from those characterized in the prior art. On the basis of these results it was decided to clone the HindIII-PstI fragment of 3 kb in the vector pUC9.

3/ Construction of the Plasmid pHT 671 Containing a Hybrid Gene of the Reconstituted Insecticidal Toxin The HindIII-HincII DNA fragment of 1.1 kb derived from the plasmid pHTE6 and the HincII-PstI DNA fragment of 1.9 kb derived from the plasmid pHTA6 are purified on agarose gels.

Figure 1:
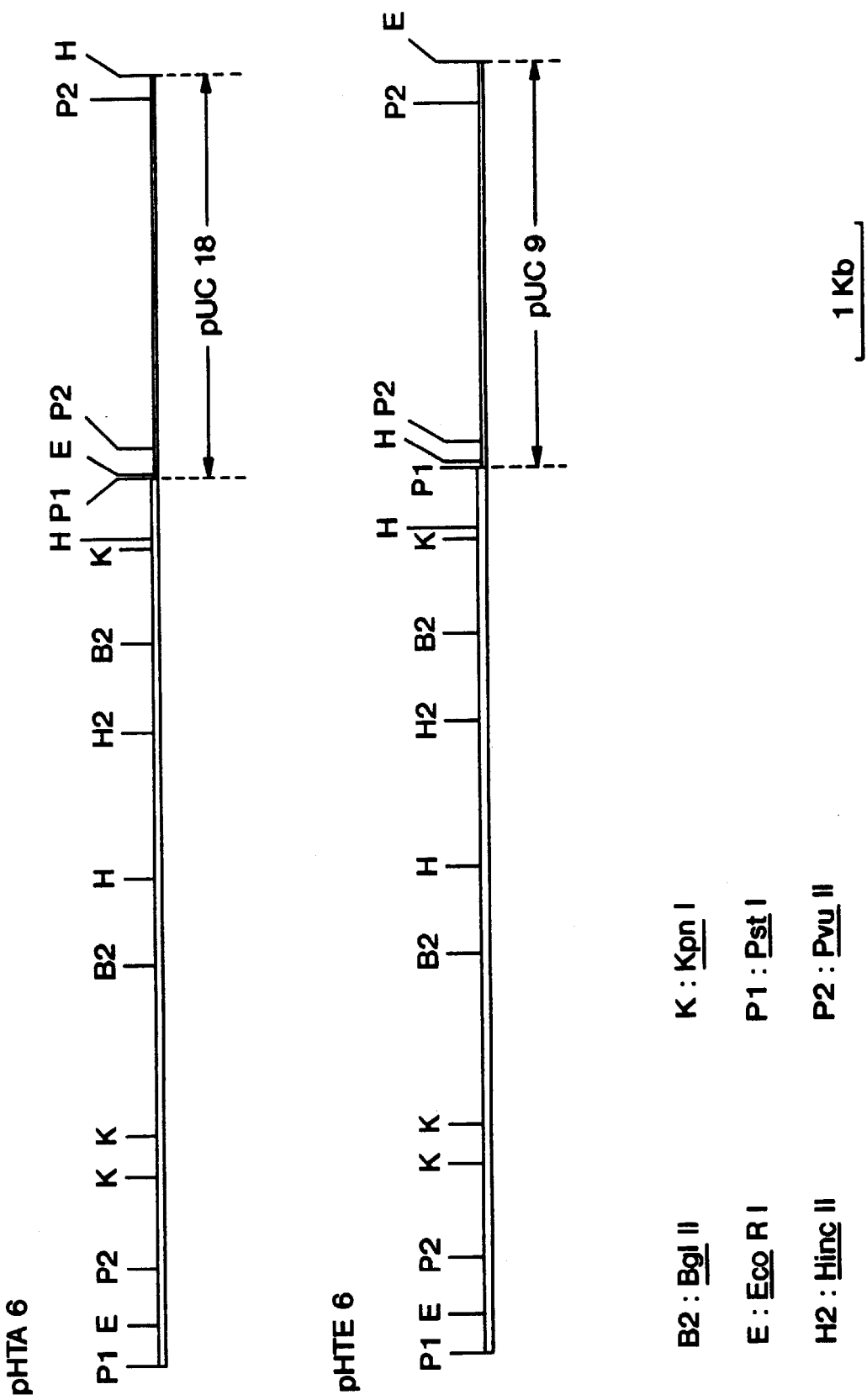
FIG. 1 presents the restriction map of the plasmids pHTA6 and pHTE6.
Figure 2:
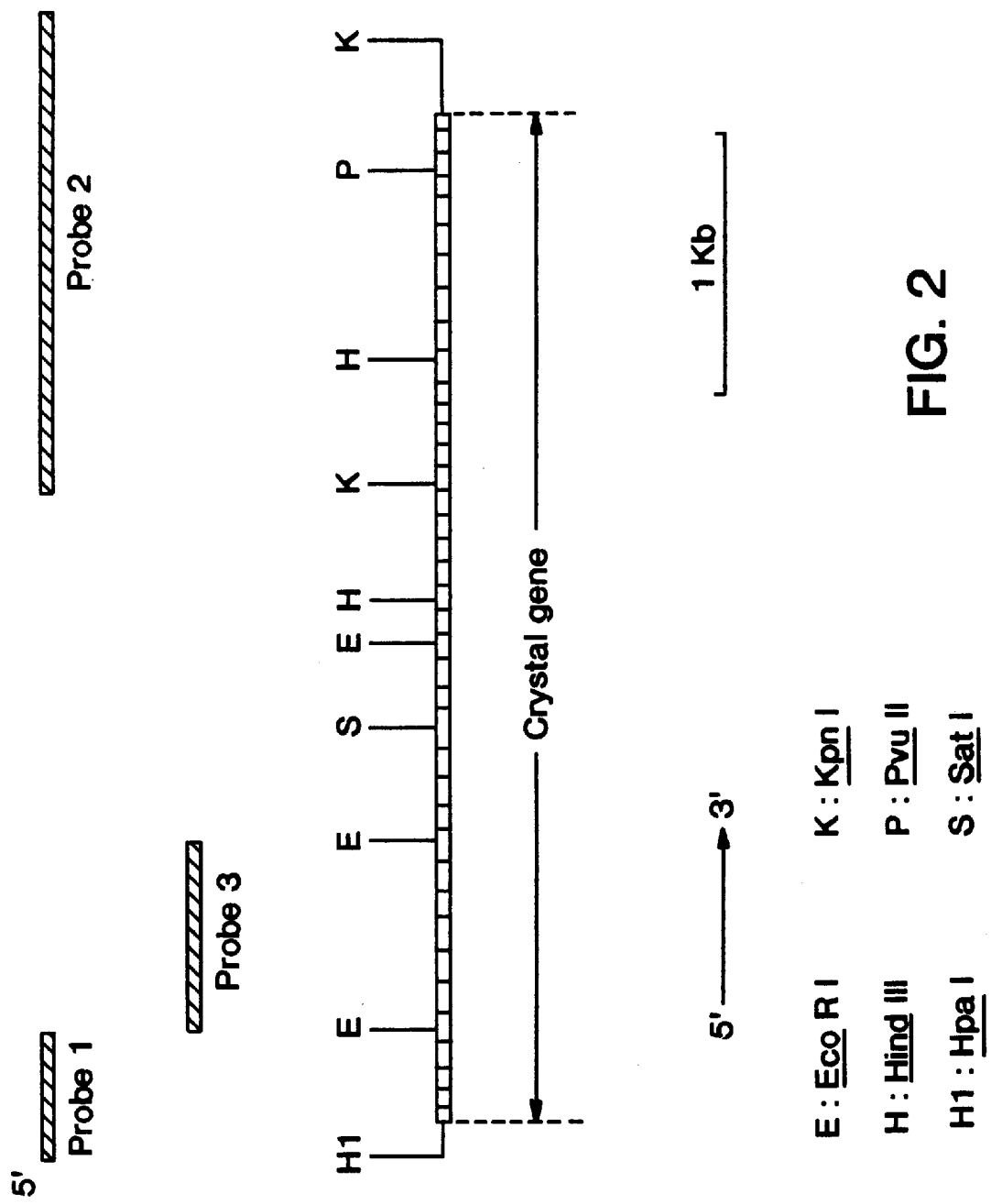
FIG. 2 depicts the restriction map of a gene for a crystal protein of the *aizawai* 7-29 strain cloned in the plasmid pHTA2 and defines the DNA fragments which are used as probes.
Figure 3:
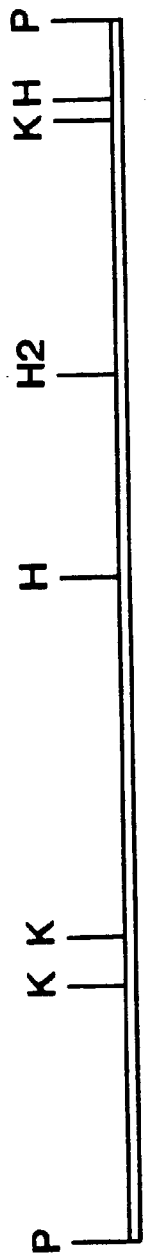
FIG. 3 shows the fragment of 6.6 kb cloned in pHTA2 and the results of a hybridization carried out between this fragment and the probes described in FIG. 2.
Figure 3:
Figure 3:
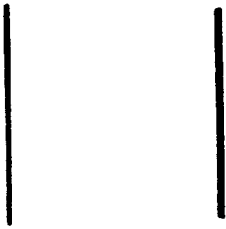
Figure 4:
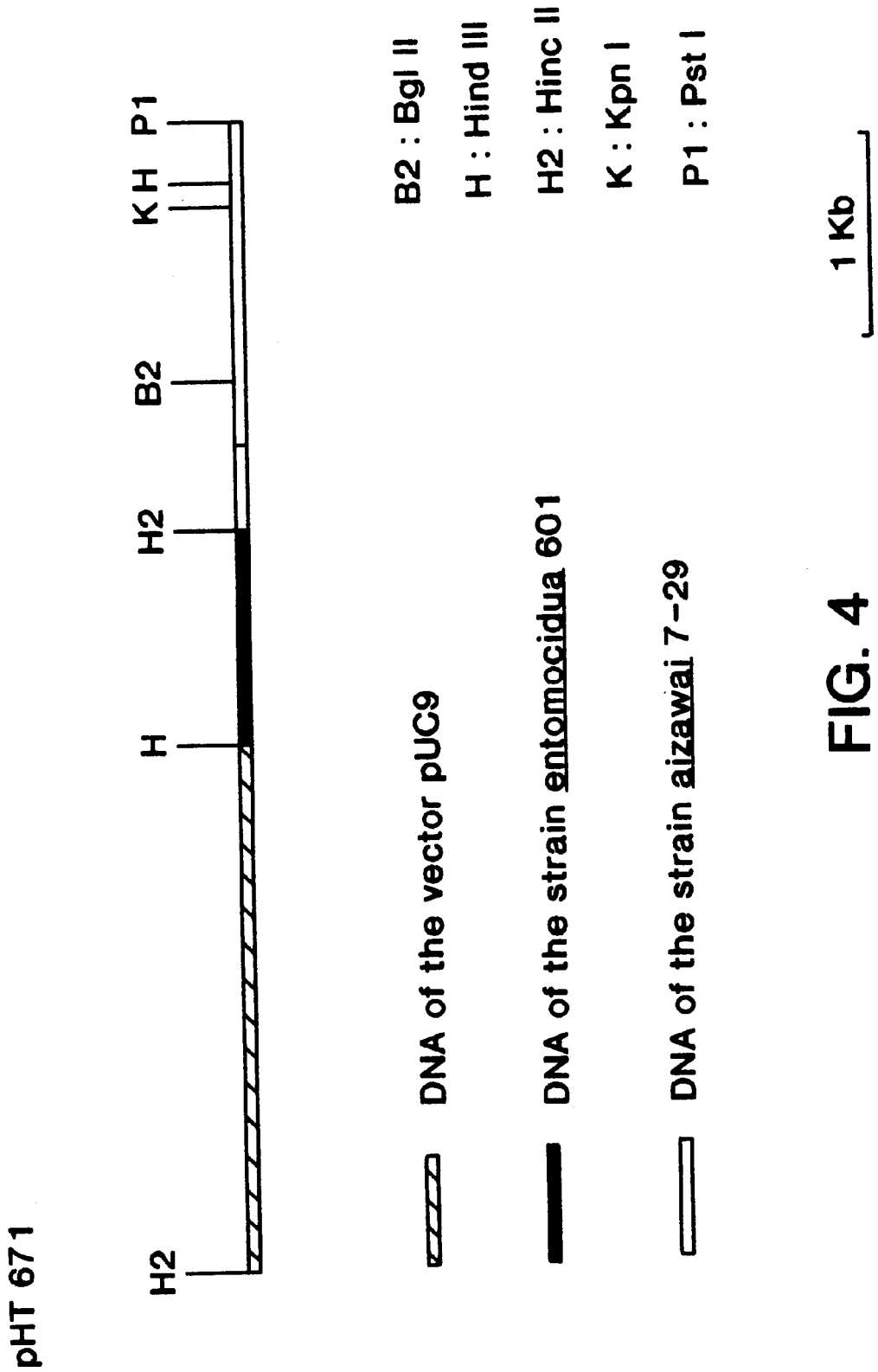
FIG. 4 depicts the restriction map of the plasmid pHT671.

Equal amounts of the two purified DNA fragments and the DNA of pUC9 digested with HindIII and PstI are mixed and ligated. The ligation mixture is used to transform competent cells of *E.coli* JM83, then the transformed *E.coli* cells are selected on LB medium containing ampicillin. One of the interesting recombinant clones examined contains a plasmid designated by pHT671, the restriction map of which was determined and is shown in FIG. 4. This plasmid (pHT671) contains a DNA fragment of 3 kb inserted in the vector pUC9. This DNA sequence has the same restriction map as the HindIII-PstI fragments of 3 kb contained in the plasmids pHTA6 and pHTE6, but corresponds to a reconstituted DNA molecule constructed by in vitro recombination from DNA sequences derived from the *aizawai* 7-29 strains on the one hand and *entomocidus* 6-01 on the other.

EXAMPLE II

Study of the Nucleotide Sequence of the Promoter Region and of the Region Coding for the NH$_2$-Terminal Part of the δ-Endotoxin Active Against the Noctuidae The HindIII-HincII fragment of pHT671 is sequenced in conformity with the method described in (8) by using a M13 system. In order to obtain partially overlapping cloned DNA fragments which will be used in the sequencing of the DNA, recourse is had to the method of subcloning by deletion in M13, developed by DALE et al (9).

The sequence of 940 nucleotides of the HindIII-HincII fragment which has a length of about 1 kilobase corresponds to the chain arrangement I above.

The analysis of this sequence shows that the largest open reading frame starts at position 241 and that a potential site of binding to the ribosomes, GGAGG, is found six base pairs upstream from this ATG codon (position 230 to 235). The region localized between the nucleotides 137 and 177 (position -103 to -63 upstream from the ATG codon) is strongly homologous with the region present upstream from the gene for the crystal of the strain *kurstaki* HD1 Dipel (BTX) sequenced by WONG et al (1983) and described in (16) and the authors of which have shown that it contains three promoters BtI, BtII, and Ec, functional in *B.thuringiensis* and *E.coli*, respectively. The comparison between the amino acid sequences deduced from the first 750 nucleotides of the genes of BTK and pHT671, show that these polypeptides exhibit significant differences at the level of the N-terminal half of the active part derived from the protoxin (only 66% strict homology). It is important to note that it is the first time that a gene for the δ-endotoxin isolated from a strain active against the Lepidoptera codes for a polypeptide which shows substantial differences in this region. In fact, this N-terminal domain appears to be strongly conserved (more than 97% of strict homology) among all of the genes for the crystal active on Lepidoptera which have been sequenced hitherto. Moreover, the inventors have shown that the degree of variability is of the same order if the nucleotide sequences of pHT671 and other genes of the Lepidoptera type are considered.

EXAMPLE III

Construction of a DNA Sequence of About 2.7 kb Containing a Gene for a Larvicidal Toxin In order to achieve this construction the DNA of the *aizawai* 7-29 strain of *B.thuringiensis* was used up to the step for the production of the plasmid pHTA6 as described in Example I.

The HindIII-PstI fragment of about 2.7 kb obtained from the plasmid pHTA6 was then subcloned in the vector pUC9, previously hydrolysed by the restriction enzymes HindIII-PstI in order to give the plasmid pHT71.

EXAMPLE IV

Study of the Sequence of Nucleotides Constituting the Plasmid pHT71 Coding for a Polypeptide Toxic Towards the Larvae of Lepidoptera of the Family of the Noctuidae The HindIII-PstI fragment of 2.7 kb of pHTA6, which was subcloned in pHT71, was sequenced by means of the technique of Sanger et al. (8) using the phage M13mp19 and the subcloning system by deletions developed by Dale et al (9). This system makes it possible to obtain M13 phages containing a series of partially overlapping DNA fragments which can be utilized for sequencing the DNA.

The sequence of nucleotides of this 2.7 kb fragment which corresponds to the chain arrangement (III) given above, was determined on the 2 DNA strands, with the. exception of the last 212 nucleotides (position 2500 to 2711) which were sequenced only on a single strand.

The nucleotide sequence of this HindIII-PstI fragment has a length of 2711 nucleotides. This fragment contains the potential promoter as well as the largest part of the gene for the δ-endotoxin active on *S.littoralis*.

EXAMPLE V

Study of the Specific Toxicity of the Recombinant Clones of *E. Coli* JM83 (pHT671) and JM83 (pHT71) Against *S.littoralis*

The toxicity of the recombinant clones of *E.coli* JM83 containing pHT671 and of *E.coli* JM83 containing pHT71 was determined by biological tests on caterpillars of the *P.brassicae* and *S.littoralis* species as described by LECADET and MARTOURET in (10). The results were compared with the specific toxicity of the native crystal proteins purified from the strains *berliner* 1715 and *aizawai* 7-29, *entomocidus* 6-01 *B.cereus* 569 (containing the plasmid pBT45, pAMβ1) against the two species of insects. The specific toxicity of the recombinant clone and of the strains of *B.thuringiensis* is expressed in terms of "specificity index" previously defined.

The results obtained are reported in table 1 below.

In this table, for *E.coli* strains, the concentration 1 corresponds to a 14 hours bacterial culture concentrated 20 times, disintegrated by ultrasound; for the *B.thuringiensis* strains the concentration is expressed in μg of crystal protein per μl of preparation. The toxic activity of the preparations was tested by the forced ingestion with 5 μl of preparation on caterpillars at the fifth stage of development, or by a technique of free ingestion utilizing larvae at the second stage of development.

TABLE 1

Comparative toxicity of a recombinant clone and two strains of *B. thuringiensis* towards *S. littoralis* and *P. brassicae.*

| | *S. littoralis* | | *P. brassicae* | Specificity index |
|---|---|---|---|---|
| Strains and plasmids | LC50 2nd larval stage | LC50 5th larval stage | LC50 5th larval stage | LC50 *S. littoralis* / LC50 *P. brassicae* |
| JM83 (pUC18) | >1 | >1 | >1 | — |
| JM83 (pHT671) | 0.04 | 0.13 | 0.72 | 0.2 |
| JM83 (pHTA2) | >1 | >1 | 0.03 | >30 |
| JM83 (pHTA4) | >1 | >1 | >1 | — |
| JM83 (pHT71) | ND | 0.5 | >1 | <0.5 |
| berliner 1715 native crystals | ND | 0.11 | 0.007 | 15.7 |
| aizawai 7.29 native crystals | ND | 0.02 | 0.04 | 0.5 |
| entomocidus 601 native crystals | ND | 0.028 | 0.012 | 2.3 |
| *B. cereus* 569 (pBT45, pAMβ 1) | ND | 0.38 | 0.054 | 7 |

Examination of the LC50 values summarized in this table 1 shows that the protein extracts of the recombinant clones JM83 (pHT671) and JM83 (pHT71) are preferentially toxic against *S.littoralis*. Secondly, a comparison of the values of the specificity index shows that the larvicidal activity of the recombinant clones is more specific by a factor of 2.5 times towards *S.littoralis* than the native crystal proteins of the *aizawai* strain. Moreover, the recombinant clones of JM83 (pHT671) and DI83 (pHT71) are very active against another insect of the family of the Noctuidae, *Mamestra brassicae* (in the case of the clone JM83 (pHT671) for example, the LC50 value is 0.02, utilizing larvae at the second stage of development).

These two results show that the gene for the larvicidal toxin constructed and cloned in the plasmids pHT671 and pHT71 codes for a protein specifically active against *S.littoralis.*

Other preparations obtained from recombinant clones containing plasmids carrying genes coding for other types of δ-endotoxins (pHTA2 and pHTA4) are not active on *S.littoralis*: it may be seen that the plasmid pHTA2 codes for a δ-endotoxin specifically active on *P.brassicae* whereas the plasmid pHTA4 codes for a δ-endotoxin, the insect target for which has not yet been identified. It can also be seen that the crystalline inclusions produced by a strain of *Bacillus cereus* which has received the plasmid pBT45, one of the plasmids of the *aizawai* 7-29 strain which also carries a δ-endotoxin gene (the gene of plasmid origin of the *aizawai* 7-29 strain), are also specifically active on *P.brassicae.*

Similar results are obtained by using, in the place of crude bacterial extracts, soluble protein extracts prepared from different recombinant clones of *E.coli.*

On the basis of the LC50 values reported in the table above and a mean individual weight of 41 mg per L5 larva (fifth larval stage) of *S.littoralis*, the value of the LD50 was estimated at 2.4 pg/gram of larva for the native crystals of the *aizawai* 7-29 strain.

On these same bases and on the basis of equivalence factors making it possible to pass from the total bacterial mass to the quantity of specific proteins (about 2% of the total proteins in *E.coli* JM83 (pHT671), the LD50 corresponding to the toxin produced by the expression in *E.coli* JM83 of the gene according to the invention cloned in the plasmid pHT671, was determined and estimated at a value close to 5.5 to 6 μg/gram of larva.

On these same bases and after determination of the LC50 of soluble protein extracts prepared from ground cultures of *E.coli* JM83 (pHT671), the value of the LD50 corresponding to the toxin present in these extracts was estimated at 4.15 μg/gram of larva.

In the two cases and particularly in the case of the ground preparations of *E.coli*, the calculated values of LD50 are approximate and higher than that of the native crystals, because it is not a question of a purified toxin. However, these data indicate without ambiguity that the gene expressed by pHT671 specifies a δ-endotoxin exhibiting the specificity towards *S.littoralis*. In fact, the same type of estimation made with extract of *E.coli* JM83 (pHTA2) carrying a δ-endotoxin gene of different specificity leads to values 30 to 50 times higher than the LD50 of the soluble extracts towards *S.littoralis* (135 to 350 μg/gram of larva).

The foregoing data will easily make it possible for the person skilled in the art to develop active larvicidal compositions with the proteins of the invention.

Other toxicity experiments were carried out utilizing larvae of *M.brassicae, S.fruqiperda* and *S.littoralis* at the second larval stage. The results obtained, expressed in terms of LC50 as defined for table 1, are given in table 2.

TABLE 2

ACTIVITY OF THE RECOMBINANT CLONES AGAINST THE LARVAE OF INSECTS OF THE FAMILY OF THE NOCTUIDAE: *M. BRASSICAE, S. FRUGIPERDA,* and *S. LITTORALIS.*

| | INSECT LARVAE AND STAGE | | |
|---|---|---|---|
| STRAINS AND PLASMIDS | *M. BRASSICAE* LC50 2nd STAGE | *S. FRUGIPERDA* LC50 2nd STAGE | *S. LITTORALIS* LC50 2nd STAGE |
| JM 83 (pUC18) | NT | NT | NT |
| JM 83 (pHTA2) | >1 | 0.51 | 0.9 |
| JM 83 (pHT671) | 0.02 | 0.5 | 0.03 |
| JM 83 (pHT71) | ND | ND | 0.03 |
| JM 83 (pHTA4) | >1 | 0.54 | >1 |

It emerges from the examination of table 2 that the crude bacterial extracts of the recombinant clone JM83 (pHT671) are toxic towards *M.brassicae* and *S.littoralis* (the values of LC50 are 0.02 and 0.03, respectively) and weakly toxic towards *S.fruqiperda* (LC50 of 0.5).

The extracts of the recombinant clone E.coli JM83 (pHTA2) are weakly active towards S.fruqiperda and S.littoralis and not at all toxic towards M.brassicae. The extracts of the recombinant clone JM83 (pHTA4) are not toxic towards M.brassicae and S.littoralis and are weakly toxic toward S.fruqiperda.

These results confirm the high specific toxicity of the proteins obtained from pHT71 and pHT671 towards S.littoralis and show that this class of crystal protein is also very active towards M.brassicae.

EXAMPLE VI

Study of the Specificity of the Polypeptides Expressed by the Clones Formed by Introduction of the Plasmids pHT671 and pHT71 into E.coli This study was carried out owing to immuno-diffusion tests. The results are reported in FIG. 5 (which includes FIGS. 5A and 5B).

The implementation of the immuno-diffusion experiment was done in conformity with the following protocol:

Soluble extracts of proteins of E.coli clones containing the plasmids pHT671, pHTA4, pHTA2 or pHT71, pUC18 were placed in the wells Nos. 2, 3, 4, 5, 6, respectively. A sample of a solubilized purified crystal of aizawai 7-29 was placed in the well No. 1 in order to serve as positive control.

Figure 5A:
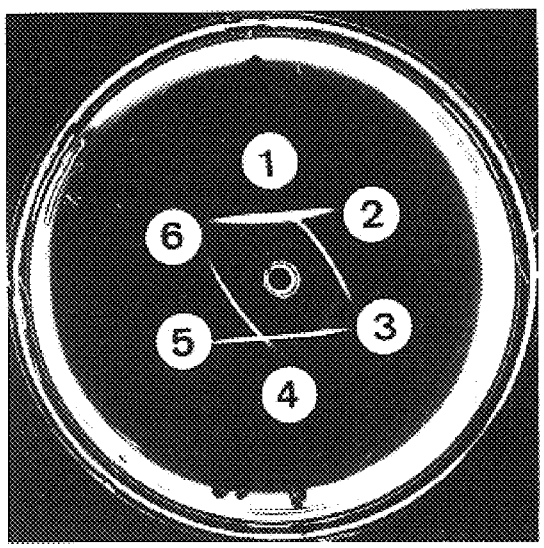
In FIG. 5A an antiserum against all of the δ-endotoxins of *aizawai* 7-29, containing rabbit antibodies directed against the solubilized crystal protein, was used in the central well.

In the test recorded in FIG. 5A an antiserum against all of the δ-endotoxins of aizawai 7-29, containing rabbit antibodies directed against the solubilized crystal proteins, was used and placed in the central well.

An immunoprecipitation line was observed in all of the cases except in the case of the extract of E.coli containing only the plasmid vector (well No. 6).

It was observed that the immuno-precipitation lines derived from the wells No. 4 and No. 5 cross, which shows that the products encoded by the plasmids pHTA2 and pHT71, respectively, display different antigenic determinants.

Figure 5B:
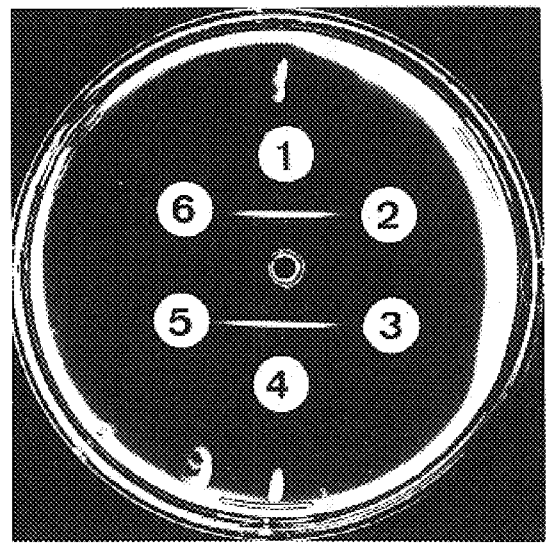
In FIG. 5B, an antiserum containing rabbit polyclonal antibodies against the crystal proteins of *Berliner* 1715 was used.

In the test recorded in FIG. 5B, the anti-serum used contained rabbit polyclonal antibodies against the crystal proteins of berliner 1715.

An immunoprecipitation line was observed with the extracts of E.coli JM83 (pHTA4) (well No. 3) JM83 (pHTA2) (well No. 4). On the other hand, the E.coli clones JM83 (pHT71) (well No. 5), JM83 (pHT671) (well No. 2) or JM83 (pUC9) (well No. 6) did not give immunoprecipitation.

It may be deduced from that that the genes for the crystal isolated in pHTA4 and pHTA2 express polypeptides having antigenic determinants in common with the proteins of the crystal of berliner 1715, a strain which is not specifically active towards S.littoralis.

On the other hand, the crude extracts of E.coli containing the plasmids pHT671 and pHT71 contain polypeptides having antigenic determinants in common with the crystal proteins of the aizawai 7-29 strain, which are not related immunogenically with the crystal proteins of the berliner 1715 strain.

These results confirm those given previously with respect to the specificity of the genes isolated in the plasmids pHT71 and pHT671.

Antigen-antibody precipitation assays have made it possible to determine the level of expression of the δ-endotoxin genes in different recombinant clones.

The results obtained have shown that the crystal protein represents between 7 and 10% of the total cellular proteins of E.coli JM83 (pHTA2), between 2 and 3% in E.coli JM83 (pHT671) and between 0.5 and 1% in E.coli JM83 (pHTA4) and E.coli JM83 (pHT71).

The literature references cited in the examples are the following:

(1) KLIER, A. F., LECADET, M-M. and DEDONDER, R., 1973, Sequential modifications of RNA polyzerase during sporogenesis in Bacillus thuringiensis, Eur. J. Biochem., 36: 317–327.
(2) MANIATIS, T., FRITSCH, E. F. , SAMBROOK, J., 1982, Molecular cloning: A laboratory manual. Cold Spring Harbor Laboratory Press, New-York
(3) VIEIRA, J. and MESSING, J., 1982, The pUC plasmids, and M13mp7 derived system for insertion mutagenesis and sequencing with synthetic universal primers, Gene, 19: 259–268.
(4) LEDERBERG, E. M. and COHEN, S. N. , 1974, Transformation of Salmonella typhimurium by plasmid deoxyribonucleic acid, J. Bacteriol., 119: 1072–1074.
(5) GRUNSTEIN, M. and HOGNESS, D. S. , 1975, Colony hybridization, a method for the isolation of cloned DNAs that contain a specific gene, Proc. Natl. Acad. Sci. U.S.A., 72: 3961–3965:
(6) SOUTHERN, E. M. , 1975, Detection of specific sequence among DNA fragments separated by gel electrophoresis, J. Molec. Biol., 98, 503–517.
(7) DENHARDT, D. T. 1976, A membrane filter taking for the detection of complementary DNA. Biochem. Biophys. Res. Comm., 23: 641–646.
(8) SANGER, F., NICKLENS, S. and COULSON, A. R. , 1977, DNA sequencing with chain terminating inhibitors. Proc. Natl. Acad. Sci. U. S. A., 74: 5463–5467.
(9) DALE et al. (1985) A rapid single-stranded cloning strategy for producing a sequential series of overlapping clones for use in DNA, Plasmid 1985, 13: 31–40
(10) LECADET.M. M. et MARTOURET D. 1987, Hcst specificity of the Bacillus thuringiensis δ-endotoxin toward Lepidopteran species: Spodoptera littoralis Bdv and Pieris brassicae L, J. of Invert. Pathol., 49 (n°1): 37–48.
(11) CHANG et al., 1979, High frequency transformation of Bacillus subtilis protoplasts by plasmid DNA-Mol Gen Genet 168:111 115
(12) HEIFRSON et al., 1987, Transformation of vegetative cells of Bacillus thuringiensis by plasmid DNA, Journal of Bacteriology, March 1987, p.1147–1152,
(13) KLIER et al., 1983, Mating between Bacillus subtilis and Bacillus thuringiensis and transfer of cloned crystal genes, Mol Gen Genet (1983) 191:257 262
(14) LERECLUS et al., 1983, Isolation of a DNA, sequence related to several plasmids from Bacillus thuringiensis after a mating involving the Streptococcus faecalis plasmid pAMβ1, Mol Gen Genet (1983) 191:307–313
(15) UMBECK et al., 1987, Genetically transformed cotton (Gossypium hirsutum L.) plants—Biotechnology vol.5 March 1987.
(16) WONG et al., 1983, transcriptional and translational start sites for the Bacillus thuringiensis crystal protein gene. J. of Biol. Chem., 258: 1960–1967.
(17) OBUKOWICZ M.et al (1986). Tn$^5$ mediated integration of the δ-endotoxin gene from B. thuringiensis into the chromosome of root colonizing Pseudomonas. J. Bacteriol., 168, 982–989.
(18) SIMON, R. et al, (1983). A broad host range mobilization system for in vivo genetic engineering: transposon mutagenesis in Gram-negative bacteria. Biotechnology, 1, pp. 784–791.
(19) Schnepf et al, (1985) The amino acid sequence of a crystal protein from *Bacillus thuringiensis* deduced from the DNA base sequence. *J BIOL Chem* 260: 6264–6372.
(20) Adang et al, (1985) characterized full-length and truncated plasmid clones of the crystal protein of *Bacillus thuringiensis* subsp. *kurstaki* HD-73 and their toxicity to Manduca sexta. Gene 46: 289–300.
(21) Wabiko et al, (1986) *Bacillus thuringiensis* entomocidal protoxin gene sequence and gene product analysis. DNA 5: 305–314.
(22) Hofte et al, (1986) Structural and functional analysis of a cloned δ-endotoxin gene of *Bacillus thuringiensis berliner* 1715. *Eur J Biochem* 161: 273–280.
(23) Shibano et al, (1986) Complete structure of an insecticidal crystal protein gene from *Bacillus thuringiensis*. In: *Bacillus molecular genetics and biotechnology applications*. J. Ganesan, A. T., Hoch, J. A.(eds). Academic Press 307–320.
(24) Oeda et al, (1987) Nucleotide sequence of the insecticidal protein gene of *Bacillus thuringiensis* strain *aizawai* IPL7 and its high-level expression in *Escherichia coli*. Gene 53: 113–119.

What is claimed is:

1. A method for obtaining a nucleotide sequence that codes for the active part of a polypeptide toxic for larvae of *S. littoralis*, wherein the method comprises:

(A) hybridizing at least one nucleotide probe to DNA from a strain of *B. thuringiensis* active against *S. littoralis*, wherein the nucleotide probe from the 5' end of a restriction fragment of a gene for δ endotoxin of *B. thuringiensis* strain *aizawa* 7-29, and wherein the nucleotide probe comprises the HincII-PstI fragment of the δ endotoxin of *B. thuringiensis* strain *aizawa* 7-29 and further comprises the HindIII-HincII restriction fragment of *B. thuringiensis* strain *entomocidus* 6-01;

(B) isolating the DNA from the strain of *B. thuringiensis* active against *S. littoralis* that hybridized to the probe;

(C) cloning the isolated DNA into a vector; and (D) purifying the vector to thereby obtain the nucleotide sequence that codes for the active part of a polypeptide toxic for larvae of *S. littoralis*.

* * * * *

UNITED STATES PATENT AND TRADEMARK OFFICE
CERTIFICATE OF CORRECTION

PATENT NO. : 6,686,149 B1  Page 1 of 1
DATED : February 3, 2004
INVENTOR(S) : Vincent Sanchis et al.

It is certified that error appears in the above-identified patent and that said Letters Patent is hereby corrected as shown below:

<u>Title page,</u>
Item [63], Related U.S. Application Data, "08/251,622," should read -- 08/251,652, --.

Signed and Sealed this

Thirtieth Day of March, 2004

JON W. DUDAS
*Acting Director of the United States Patent and Trademark Office*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2711 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
AAGCTTCAAT AGAATCTCAA ATCTCGATGA CTGCTTAGTC TTTTTAATAC TGTCTACTTG      60

ACAGGGGTAG GAACATAATC GGTCAATTTT AAATATGGGG CATATATTGA TATTTTATA      120

AATTTGTTAC GTTTTTTGTA TTTTTTCATA AGATGTGTCA TATGTATTAA ATCGTGGTA      180

TGAAAAACAG TATCAAACTA TCAGAACTTT GGTAGTTTAA TAAAAAAACG GAGGTATTT      240

ATGGAGGAAA ATAATCAAAA TCAATGCATA CCTTACAATT GTTTAAGTAA TCCTGAAGA      300

GTACTTTTGG ATGGAGAACG GATATCAACT GGTAATTACT CAATTGATAT TTCTCTGTC      360

CTTGTTCAGT TTCTGGTATC TAACTTTGTA CCAGGGGGAG GATTTTTAGT TGGATTAAT      420

GATTTTGTAT GGGGAATAGT TGGCCCTTCT CAATGGGATG CATTTCTAGT ACAAATTGA      480

CAATTAATTA ATGAAAGAAT AGCTGAATTT GCTAGGAATG CTGCTATTGC TAATTTAGA      540

GGATTAGGAA ACAATTTCAA TATATATGTG GAAGCATTTA AGAATGGGA AGAAGATCC       600

AATAATCCAG CAACCAGGAC CAGAGTAATT GATCGCTTTC GTATACTTGA TGGGCTACT      660

GAAAGGGACA TTCCTTCGTT TCGAATTTCT GGATTTGAAG TACCCCTTTT ATCCGTTTA      720

GCTCAAGCGG CCAATCTGCA TCTAGCTATA TTAAGAGATT CTGTAATTTT TGGAGAAAG      780

TTGGGATTGA CAACGATAAA TGTCAATGAA AACTATAATA GACTAATTAG GCATATTGA      840

GAATATGCTG ATCACTGTGC AAATACGTAT AATCGGGGAT TAAATAATTT ACCGAAATC      900

ACGTATCAAG ATTGGATAAC ATATAATCGA TTACGGAGAG ACTTAACATT GACTGTATT      960

GATATCGCCG CTTTCTTTCC AAACTATGAC AATAGGAGAT ATCCAATTCA GCCAGTTG     1020

CAACTAACAA GGGAAGTTTA TACGGACCCA TTAATTAATT TTAATCCACA GTTACAGT     1080

GTAGCTCAAT TACCTACTTT TAACGTTATG GAGAGCAGCG CAATTAGAAA TCCTCATT    1140
```

-continued

```
TTTGATATAT TGAATAATCT TACAATCTTT ACGGATTGGT TTAGTGTTGG ACGCAATT      1200

TATTGGGGAG GACATCGAGT AATATCTAGC CTTATAGGAG GTGGTAACAT AACATCTC      1260

ATATATGGAA GAGAGGCGAA CCAGGAGCCT CCAAGATCCT TTACTTTTAA TGGACCGG      1320

TTTAGGACTT TATCAATTCC TACTTTACGA TTATTACAGC AACCTTGCCA GCGCCACC      1380

TTTAATTTAC GTGGTGGTGA AGGAGTAGAA TTTTCTACAC CTACAAATAG CTTTACGT      1440

GCAGGAAGAG GTACGGTTGA TTCTTTAACT GAATTACCGC CTGAGGATAA TAGTGTGC      1500

CCTCGCGAAG GATATAGTCA TCGTTTATGT CATGCAACTT TGTTCAAAG ATCTGGAA       1560

CCTTTTTTAA CAACTGGTGT AGTATTTTCT TGGACGCATC GTAGTGCAAC TCTTACAA      1620

ACAATTGATC CAGAGAGAAT TAATCAAATA CCTTTAGTGA AAGGATTTAG AGTTTGGG      1680

GGCACCTCTG TCATTACAGG ACCAGGATTT ACAGGAGGGG ATATCCTTCG AAGAAATA      1740

TTTGGTGATT TTGTATCTCT ACAAGTCAAT ATTAATTCAC CAATTACCCA AAGATACC      1800

TTAAGATTTC GTTACGCTTC CAGTAGGGAT GCAGCAGTTA TAGTATTAAC AGGAGCGG      1860

TCCACAGGAG TGGGAGGCCA AGTTAGTGTA GATATGCCTC TTCAGAAAAC TATGGAAA      1920

GGGGAGAACT TAACATCTAG AACATTTAGA TATACCGATT TTAGTAATCC TTTTTCAT      1980

AGAGCTAATC CAGATATAAT TGGGATAAGT GAACAACCTC TATTTGGTGC AGGTTCTA      2040

AGTAGCGTTG AACTTTATAT AGATAAAATT GAAATTATTC TAGCAGATGC AACATTTG      2100

GCAGAATCTG ATTTAGAAAG AGCACAAAAG GCGGTGAATG CCCTGTTTAC TTCTTCCA      2160

CAAATCGGGT TAAAAACCGA TGTGACGGAT TATCATATTG ATCAAGTATC CAATTTAG      2220

GATTGTTTAT CAGATGAATT TTGTCTGGAT GAAAAGCGAG AATTGTCCGA GAAAGTCA      2280

CATGCGAAGC GACTCAGTGA TGAGCGGAAT TTACTTCAAG ATCCAAACTT CAGAGGGA      2340

AATAGACAAC CAGACCGTGG CTGGAGAGGA AGTACAGATA TTACCATCCA AGGAGGAG      2400

GACGTATTCA AAGAGAATTA CGTCACACTA CCGGGTACCG TTGATGAGTG CTATCCAA      2460

TATTTATATC AGAAAATAGA TGAGTCGAAA TTAAAAGCTT ATACCCGTTA TGAATTAA      2520

GGGTATATCG AAGATAGTCA AGACTTAGAA ATCTATTTGA TCGCGTACAA TGCAAAAC      2580

GAAATAGTAA ATGTGCCAGG CACGGGTTCC TTATGGCCGC TTTCAGCCCA AAGTCCAA      2640

GGAAAGTGTG GAGAACCGAA TCGATGCGCG CCACACCTTG AATGGAATCC TGATCTAG      2700

TGTTCCTGCA G                                                          2711
```

(2) INFORMATION FOR SEQ ID NO: 2:

(i) SEQUENCE CHARACTERISTICS:
        (A) LENGTH: 823 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO: 2:

```
Met Glu Glu Asn Asn Gln Asn Gln Cys Ile Pro Tyr Asn Cys Leu Se
1               5                   10                  15

Asn Pro Glu Glu Val Leu Leu Asp Gly Glu Arg Ile Ser Thr Gly As
            20                  25                  30

Ser Ser Ile Asp Ile Ser Leu Ser Leu Val Gln Phe Leu Val Ser As
        35                  40                  45

Phe Val Pro Gly Gly Gly Phe Leu Val Gly Leu Ile Asp Phe Val Tr
    50                  55                  60
```

```
Gly Ile Val Gly Pro Ser Gln Trp Asp Ala Phe Leu Val Gln Ile Gl
 65                  70                  75                  80

Gln Leu Ile Asn Glu Arg Ile Ala Glu Phe Ala Arg Asn Ala Ala Il
                 85                  90                  95

Ala Asn Leu Glu Gly Leu Gly Asn Asn Phe Asn Ile Tyr Val Glu Al
                100                 105                 110

Phe Lys Glu Trp Glu Asp Pro Asn Asn Pro Ala Thr Arg Thr Ar
            115                 120                 125

Val Ile Asp Arg Phe Arg Ile Leu Asp Gly Leu Leu Glu Arg Asp Il
130                 135                 140

Pro Ser Phe Arg Ile Ser Gly Phe Glu Val Pro Leu Leu Ser Val Ty
145                 150                 155                 160

Ala Gln Ala Ala Asn Leu His Leu Ala Ile Leu Arg Asp Ser Val Il
                165                 170                 175

Phe Gly Glu Arg Trp Gly Leu Thr Thr Ile Asn Val Asn Glu Asn Ty
            180                 185                 190

Asn Arg Leu Ile Arg His Ile Asp Glu Tyr Ala Asp His Cys Ala As
        195                 200                 205

Thr Tyr Asn Arg Gly Leu Asn Asn Leu Pro Lys Ser Thr Tyr Gln As
    210                 215                 220

Trp Ile Thr Tyr Asn Arg Leu Arg Arg Asp Leu Thr Leu Thr Val Le
225                 230                 235                 240

Asp Ile Ala Ala Phe Phe Pro Asn Tyr Asp Asn Arg Arg Tyr Pro Il
                245                 250                 255

Gln Pro Val Gly Gln Leu Thr Arg Glu Val Tyr Thr Asp Pro Leu Il
            260                 265                 270

Asn Phe Asn Pro Gln Leu Gln Ser Val Ala Gln Leu Pro Thr Phe As
        275                 280                 285

Val Met Glu Ser Ser Ala Ile Arg Asn Pro His Leu Phe Asp Ile Le
    290                 295                 300

Asn Asn Leu Thr Ile Phe Thr Asp Trp Phe Ser Val Gly Arg Asn Ph
305                 310                 315                 320

Tyr Trp Gly Gly His Arg Val Ile Ser Ser Leu Ile Gly Gly As
                325                 330                 335

Ile Thr Ser Pro Ile Tyr Gly Arg Glu Ala Asn Gln Glu Pro Pro Ar
            340                 345                 350

Ser Phe Thr Phe Asn Gly Pro Val Phe Arg Thr Leu Ser Ile Pro Th
        355                 360                 365

Leu Arg Leu Leu Gln Gln Pro Cys Gln Arg His His Phe Asn Leu Ar
    370                 375                 380

Gly Gly Glu Gly Val Glu Phe Ser Thr Pro Thr Asn Ser Phe Thr Ty
385                 390                 395                 400

Arg Gly Arg Gly Thr Val Asp Ser Leu Thr Glu Leu Pro Pro Glu As
                405                 410                 415

Asn Ser Val Pro Pro Arg Glu Gly Tyr Ser His Arg Leu Cys His Al
            420                 425                 430

Thr Phe Val Gln Arg Ser Gly Thr Pro Phe Leu Thr Thr Gly Val Va
        435                 440                 445

Phe Ser Trp Thr His Arg Ser Ala Thr Leu Thr Asn Thr Ile Asp Pr
    450                 455                 460

Glu Arg Ile Asn Gln Ile Pro Leu Val Lys Gly Phe Arg Val Trp Gl
465                 470                 475                 480

Gly Thr Ser Val Ile Thr Gly Pro Gly Phe Thr Gly Gly Asp Ile Le
```

-continued

```
                              485                   490                    495
Arg Arg Asn Thr Phe Gly Asp Phe Val Ser Leu Gln Val Asn Ile As
            500                   505                    510
Ser Pro Ile Thr Gln Arg Tyr Arg Leu Arg Phe Arg Tyr Ala Ser Se
            515                   520                    525
Arg Asp Ala Arg Val Ile Val Leu Thr Gly Ala Ala Ser Thr Gly Va
        530                   535                    540
Gly Gly Gln Val Ser Val Asn Met Pro Leu Gln Lys Thr Met Glu Il
545                   550                   555                    560
Gly Glu Asn Leu Thr Ser Arg Thr Phe Arg Tyr Thr Asp Phe Ser As
                565                   570                    575
Pro Phe Ser Phe Arg Ala Asn Pro Asp Ile Ile Gly Ile Ser Glu Gl
            580                   585                    590
Pro Leu Phe Gly Ala Gly Ser Ile Ser Ser Gly Glu Leu Tyr Ile As
            595                   600                    605
Lys Ile Glu Ile Ile Leu Ala Asp Ala Thr Phe Glu Ala Glu Ser As
        610                   615                    620
Leu Glu Arg Ala Gln Lys Ala Val Asn Ala Leu Phe Thr Ser Ser As
625                   630                   635                    640
Gln Ile Gly Leu Lys Thr Asp Val Thr Asp Tyr His Ile Asp Gln Va
                645                   650                    655
Ser Asn Leu Val Asp Cys Leu Ser Asp Glu Phe Cys Leu Asp Glu Ly
            660                   665                    670
Arg Glu Leu Ser Glu Lys Val Lys His Ala Lys Arg Leu Ser Asp Gl
            675                   680                    685
Arg Asn Leu Leu Gln Asp Pro Asn Phe Arg Gly Ile Asn Arg Gln Pr
        690                   695                    700
Asp Arg Gly Trp Arg Gly Ser Thr Asp Ile Thr Ile Gln Gly Gly As
705                   710                   715                    720
Asp Val Phe Lys Glu Asn Tyr Val Thr Leu Pro Gly Thr Val Asp Gl
                725                   730                    735
Cys Tyr Pro Thr Tyr Leu Tyr Gln Lys Ile Asp Glu Ser Lys Leu Ly
            740                   745                    750
Ala Tyr Thr Arg Tyr Glu Leu Arg Gly Tyr Ile Glu Asp Ser Gln As
            755                   760                    765
Leu Glu Ile Tyr Leu Ile Ala Tyr Asn Ala Lys His Glu Ile Val As
        770                   775                    780
Val Pro Gly Thr Gly Ser Leu Trp Pro Leu Ser Ala Gln Ser Pro Il
785                   790                   795                    800
Gly Lys Cys Gly Glu Pro Asn Arg Cys Ala Pro His Leu Glu Trp As
                805                   810                    815
Pro Asp Leu Asp Cys Ser Cys
                820
```